United States Patent
Aberg et al.

(10) Patent No.: US 6,207,683 B1
(45) Date of Patent: Mar. 27, 2001

(54) BENZOCYCLOHEPTATHIOPHENE COMPOUNDS

(75) Inventors: A. K. Gunnar Aberg, Sarasota, FL (US); George E. Wright; Jan L. Chen, both of Worcester, MA (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 09/381,351

(22) PCT Filed: Apr. 2, 1998

(86) PCT No.: PCT/US98/06576

§ 371 Date: Oct. 29, 1999

§ 102(e) Date: Oct. 29, 1999

(87) PCT Pub. No.: WO98/43640

PCT Pub. Date: Oct. 8, 1998

Related U.S. Application Data

(60) Provisional application No. 60/043,905, filed on Apr. 3, 1997.

(51) Int. Cl.$^7$ .................................................. A61K 31/445
(52) U.S. Cl. .................................. 514/324; 546/202
(58) Field of Search ........................... 514/324; 546/202

(56) References Cited

U.S. PATENT DOCUMENTS

| 4,355,036 | 10/1982 | Villani ................................. 424/267 |
| 5,250,681 | 10/1993 | Shoji et al. ............................ 540/577 |

OTHER PUBLICATIONS

Yasuo et al, Chemical Abstracts, vol. 116. #83546v, 1992.*

* cited by examiner

*Primary Examiner*—James H. Reamer
(74) *Attorney, Agent, or Firm*—Nields & Lemack

(57) ABSTRACT

Disclosed are N-substituted hydroxyalkyl or carboxyalkyloxyalkyl analogs of 9- and/or 10-oxo-4Hbenzo[4,5]cycloheptal[1,2-b]thiophene compounds, or 9-OH and/or 10-OH-substituted analogs thereof, which possess antihistaminic and antiasthmatic properties with reduced sedative side effects. The optically active isomers and pharmaceutically acceptable salts thereof are also described. The compounds were also found to prevent smooth muscle hyperreactivity.

20 Claims, No Drawings

US 6,207,683 B1

BENZOCYCLOHEPTATHIOPHENE COMPOUNDS

This application is a 371 of PCT/US98/06576, filed Apr. 2, 1998 which claims benefit of application Ser. No. 60/043,905 filed Apr. 3, 1997.

TECHNICAL FIELD

This invention relates to new chemical entities as shown below and to methods of treatment of disease states modulated by allergic, inflammatory, or cholinergic activities in a mammal, using said new chemical entities.

The compounds of the invention include chemical entities of the following formula:

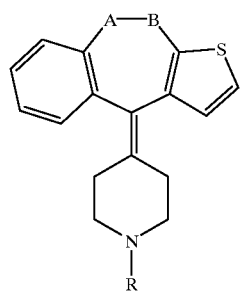

where
—A—B— is a moiety having the formula

| | |
|---|---|
| —CO—CH$_2$— | (a) |
| —CH$_2$—CO— | (b) |
| —CH$_2$—CH$_2$— | (c) |
| —CHOH—CH$_2$— | (d) |
| —CHOH—CHOH— | (e) |
| —CH$_2$—CHOH— | (f) | or

| | |
|---|---|
| —CO—CO— | (g) and | where
R is a hydroxyalkyl or a carboxyalkyloxyalkyl moiety, and the pharmaceutically acceptable salts thereof, and the optically active isomers of the racemic compounds.

The compounds of this inventions have pharmacological properties that render said compounds to be useful in preventing and treating allergies, inflammations, various types of ocular diseases, and different types of smooth muscle hyperreactivity (such as bronchial and uterine hyperreactivity, including drug-induced hyperreactivity).

More particularly, this invention relates to new chemical entities and to methods of treating allergic disorders (such as for example allergic rhinitis), pulmonary disorders (such as for example asthma, bronchitis, cough and bronchial hyperreactivity), skin disorders (such as for example urticaria, psoriasis and atopic dermatitis), gastro-intestinal disorders (such as hypersecretory syndromes including Zollinger-Ellison syndrome, gastric irritation and enteritis) and other inflammatory disorders and/or allergic disorders (such as for example ocular conjunctivitis and ocular keratitis), while avoiding side effects (such as sedation, cardiac arrhythmias and ocular irritation), using said new chemical entities.

The invention also refers to compositions, containing at least one of said new chemical entities and combination of the present compounds with various other chemical entities.

BACKGROUND OF THE INVENTION

This invention relates specifically to anti-inflammatory and anti-allergic compounds, having therapeutic use in various diseases, most importantly for patients suffering from hyperreactive airways and/or obstructive airways diseases, including asthma and bronchitis or from skin disorders and allergies, including urticaria, atopic dermatitis, allergic rhinitis and retinopathy or other small vessel diseases associated with diabetes mellitus or from ocular disorders, including conjunctivitis and keratitis.

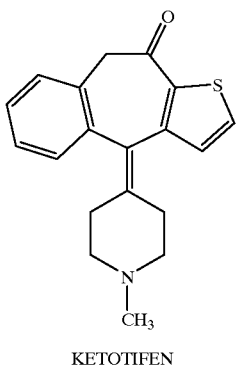

KETOTIFEN

The present compounds demonstrate chemical similarities to ketotifen (Zaditen®) and are not previously known to the applicants. Sedative side effects have severely limited the therapeutic usefulness of ketotifen and such side effects can been reduced or eliminated by using the compounds of the present invention.

The pharmacology, toxicology, metabolism and the clinical experience with ketotifen has been summarized by Sorkin et al. (Focus on Ketotifen. Ed. E. M. Sorkin. *In Drugs,* September 1990, Vol. 40, No. 3, pp. 412–448).

SUMMARY OF THE INVENTION

The present invention is concerned with certain new chemical entities as described below, methods of using said chemical entities for therapeutic purposes and compositions comprising one or more pharmaceutically acceptable inert carriers and as active ingredient a therapeutically effective amount of at least one compound, the pharmaceutically acceptable acid addition salts thereof and the stereochemically isomeric forms thereof, having the formula:

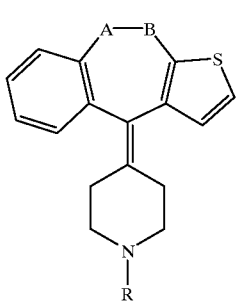

where
R is a member selected from the group consisting of hydroxy-C$_{2-6}$alkyl or carboxy-C$_{1-6}$alkyloxy-C$_{1-6}$alkyl and —A—B— is a moiety having the formula —CO—CH$_2$— (a)

—CH$_2$—CO— (b)

—CH$_2$—CH$_2$— (c)

—CHOH—CH$_2$— (d)

—CHOH—CHOH— (e)

—CH$_2$—CHOH— (f)

or

—CO—CO— (g)

Compounds of the present invention have been synthesized and studied pharmacologically. Significant pharmacological differences were found between the compounds of the present invention and ketotifen. Thus, ketotifen has profound sedative side effects while the present compounds have now been found to have reduced or no sedative activity. It has also been established that the new compounds have anti-histaminergic and anti-inflammatory properties. Of importance is that the new compounds have potent pulmonary anti-inflammatory effects and that they potently inhibit bronchial smooth muscle hyperreactivity.

Since pulmonary airway inflammation and bronchial smooth muscle hyperreactivity are the hallmarks of asthma, it is concluded that the new compounds—in additions to being potent antihistamines—will have clinical utility for the treatment of asthma and bronchitis, without concomitant sedative side effects.

DETAILED DESCRIPTION BIOLOGICAL STUDIES OF THE COMPOUNDS OF THE PRESENT INVENTION

As discussed above, it is now shown that the compounds of the present invention have beneficial pharmacological effects, useful in the treatment of various disorders, such as asthma, allergies and ocular disorders. The new findings are described in the following biological studies.

1. Binding to histaminergic receptors

The affinities of the test compounds for histamine H$_1$-receptors were assessed using the [$^3$H]pyrilamine binding assay, modified after Chang et al. Heterogeneity of Histamine H$_1$-Receptors. J. Neurochem. 1979, 32: 1653–1663 Briefly, membranes from bovine cerebellum were incubated with [$^3$H]pyrilamine and the test compound at increasing concentrations. The specific binding of the radioactive ligand to the receptor was defined as the difference between total binding and nonspecific binding, determined in the presence of an excess of unlabelled ligand. IC$_{50}$ values (concentration required to inhibit 50% of specific binding of [$^3$H]pyrilamine) were determined by non linear regression analysis of the competition curves.

|  | IC50 (M) |
|---|---|
| KETOTIFEN | 8.15 × 10−9 |
| NORKETOTIFEN | 4.36 × 10−8 |
| 10-OH-NORKETOTIFEN | 1.13 × 10−7 |
| EXAMPLE 2, where n = 2 | 5.85 × 10−9 |
| EXAMPLE 5, where n = 2 | 6.95 × 10−8 |
| TRIPROLIDINE HCl (reference compound) | 1.41 × 10−8 |

2. Binding to muscarinic receptors

The affinities of the test compounds for muscarinic M$_1$-receptors were assessed using the [$^3$H]pirenzepine binding assay, modified after Luthin et al. [$^3$H]Pirenzepine and [$^3$H]QNB binding to brain muscarinic cholinergic receptors. Molec. Pharmac. 1984, 26: 164–169. Briefly, the experiments were carried out on bovine striatal membranes expressing muscarinic M$_1$-receptors. After incubation with the test article and the proper radioligand and washing, bound radioactivity is determined with a ligand scintillation counter, using a commercial scintillation cocktail. The specific radioligand binding to each receptor is defined as the difference between total binding and nonspecific binding determined in the presence of an excess of unlabelled ligand. IC$_{50}$ values (concentrations required to inhibit 50% of specific binding) were determined by non linear regression analysis of the competition curves.

|  | IC 50 (M) |
|---|---|
| KETOTIFEN | 7.11 × 10−8 |
| NORKETOTIFEN | 2.61 × 10−7 |
| EXAMPLE 2, where n = 2 | 2.35 × 10−7 |
| EXAMPLE 5, where n = 2 | 8.80 × 10−7 |
| ATROPINE Sulfate (reference compound) | 5.74 × 10−10 |

3. Studies on sedative effects

The physostigmine-induced lethality test used in these tests is a modification of the sedation test technique reported by COLLIER et al., in Br. J. Pharmac., 1968, 32: 295–310. In short, physostigmine (1.9 mg/kg s.c.) produces 100% lethality when given to grouped mice with 10 animals in each plastic cage (approx. 11×26×13 cm). Mice administered a sedating antihistamine prior to physostigmine are protected and survive. In the present study, test compounds were administered orally 60 minutes prior to physostigmine. The number of survivors were counted 30 minutes after physostigmine administration. The doses in the CNS test were half of the molecular weights of the test compounds, expressed in mg/kg body weight.

| Oral treatment (mg/kg) | Survived |
|---|---|
| Ketotifen (107) | 9/10 |
| Nor-ketotifen (83) | 3/10 |
| EXAMPLE 2, where n = 2 (94) | 3/10 |
| EXAMPLE 5, where n = 2 (108 ) | 0/10 |
| Vehicle | 0/10 |
| Astemizole (115) | 1/10 |
| Non-sedating antihistamine reference compound | |

4. Antiinflammatory effects (inhibition of bronchial eosinophil accumulation)

Inhibition of eosinophil accumulation in lung is determined in guinea pigs (400 to 600 grams) following intraperitoneal injection of 10 μg PAF (platelet aggregating factor) in 0.25% bovine serum albumin in saline. Twenty-four hours later the animals are killed with barbiturate. The trachea is exposed and cannulated. 6×10 ml aliquots of buffered modified Tyrode's solution (composition: NaHCO$_3$ 11.9, NaCl 136.9, KCl 2.7, Na$_2$HPO$_4$ 0.4, glucose 5.6, EDTA 19.8, gelatin 0.1% w/v, BSA 0.5% w/v; pH 7.4) are introduced successively and aspirated by gentle compression of the lungs. Total fluid recovery normally exceeded 80%. Cell suspensions are concentrated by low speed centrifugation and the resulting cell pellet is resuspended in 1 ml Tyrode's solution. Total cell counts are made by diluting 10 μl of cell suspension in 90 μl of Turk's fluid. Differential cell counts are made from smears fixed in methanol (100%) and stained in Leishman stain. A total of at least 500 cells per smear are counted at 1000 fold magnification, in order to differentiate cell types. Drugs are administered for 7 days as a sustained subcutaneous infusion from an implanted Alza minipump so that exposure to PAF occurs only after a five day pretreatment period with the test compound(s).

5. Studies on gastric effects

The effects of the compounds of the inventions are studied on bradykinin-induced contractions of the isolated guinea pig ileum. The tissue is pretreated with various concentrations of the test compounds before the contractile responses to bradykinin (in the absence or presence of atropine 1 μM).

The effects of the compounds on gastric ulcerations are studied in the rat. Ulcerations are produced by s.c. injection of 30 mg/kg of indomethacin. Study groups received test compounds 100 μg/100 g body. weight, p.o., 30 min. before and 5 hours after indomethacin administration. The reduction of ulcer area is measured (mm$^2$).

CHEMICAL SYNTHESIS OF NEW COMPOUNDS. EXAMPLES

The synthesis of ketotifen, nor-ketotifen and of (RS)-10-OH-ketotifen have been described by Waldvogel et al. (Helv Chem Acta, 1976, 59:866–877), the subject matters of which are incorporated herein by reference.

The new compounds of the present invention are of the general formula, shown in Table 1, below.

The starting compounds for these syntheses are obtained as described in Waldvogel et al.:

Compound (1) 4-(4-piperidylidene)-9,10-dihydro-4 H-benzo[4,5]cyclo-hepta[1,2-b] thiophene-9-one.

Compound (2) 4-(4-piperidylidene)-9,10-dihydro-4 H-benzo[4,5]cyclo-hepta[1,2-] thiophene-10-one.

Compound (3) 40(4-piperidylidene)-9,10-dihydro-4 H-benzo[4,5]cyclo-hepta[1,2-b] thiophene.

Compound (4) 4-(4-piperidylidene)-9,10-dihydro-4 H-benzo[4,5]cyclo-hepta[1,2-b] thiophene-9,10-dione.

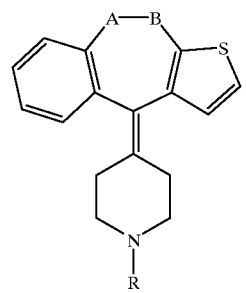

where

R is a member selected from the group consisting of hydroxy-$C_{2-6}$alkyl or carboxy-$C_{1-6}$alkyloxy-$C_{1-6}$alkyl, and —A—B— is a moiety having the formula —CO—CH$_2$—    (a)

—CH$_2$—CO—    (b)

—CH$_2$—CH$_2$—    (c)

—CHOH—CH$_2$—    (d)

—CHOH—CHOH—    (e)

—CH$_2$—CHOH—    (f)

or

—CO—CO—    (g)

Table 1. New compounds of the present invention.

EXAMPLE 1

The compound of Table 1, wherein R is —(CH$_2$)$_n$OH and wherein —A—B— has the formula —CO—CH$_2$—, and wherein n=2, is prepared by treatment of starting Compound (1) with a 2-haloethanol, such as 2-bromoethanol or 2-chloroethanol, in presence of a basic catalyst such as potassium carbonate in a solvent such as N,N-dimethylformamide (DMF) with stirring with or without heating to cause reaction. After removal of the solvent by evaporation, the residue is mixed with water and extracted with an organic solvent such as chloroform, methylene chloride or ethyl acetate. After removal of the organic solvent by evaporation, the product may be purified by crystallization from a solvent such as methanol or ethanol. Similar compounds, where n=3–6, may be prepared by the same method but with use of ω-halo alcohols, X—(CH$_2$)$_{3-6}$—OH, where X is chloro or bromo.

The products may be converted to the hydrochloride salts by dissolving in a solvent mixture such as chloroform/diethyl ether and adding a solution of hydrogen chloride in dioxane. Evaporation of the solvents yields the product as the hydrochloride.

EXAMPLE 2

The compound of Table 1, wherein R is —(CH$_2$)$_n$OH and wherein —A—B— has the formula —CH$_2$—CO—, and wherein n=2, was prepared by reaction of one gram of Compound (2) with a 2-chloroethanol (3 equivalents), potassium carbonate (3 equivalents) and potassium iodide (0.4 equivalent) in 10 ml of dimethylformamide. After stirring for four days at room temperature, the solvent was evaporated in vacuo, the residue was dissolved in chloroform (50 ml), and the solution was washed with water and dried with magnesium sulfate. The solvent was removed and the crude product was purified by chromatography on silica gel with 5% methanol in chloroform as eluent. The product was dissolved in chloroform/diethyl ether, and a solution of hydrogen chloride in dioxane was added. The solvents were evaporated in vacuo leaving Example 2 (n=2) as the hydrochloride. Yield: 0.87gram. Proton NMR was consistent with the proposed structure.

EXAMPLE 3

The compound of Table 1, wherein R is —(CH$_2$)$_n$OH and wherein —A—B— has the formula —CH$_2$—CH$_2$—, and wherein n=2, is prepared by treatment of starting Compound (3) with a 2-haloethanol, such as 2-bromoethanol or 2-chloroethanol, in presence of a basic catalyst such as potassium carbonate in a solvent such as N,N-dimethylformamide (DMF) with stirring with or without heating to cause reaction. After removal of the solvent by evaporation, the residue is mixed with water and extracted with an organic solvent such as chloroform, methylene chloride or ethyl acetate. After removal of the organic solvent by evaporation, the product may be purified by crystallization from a solvent such as methanol or ethanol. Similar compounds, where n=3–6, may be prepared by the same method but with ω-halo alcohols, X—(CH$_2$)$_{3-6}$—OH, where X is chloro or bromo.

The products may be converted to the hydrochloride slats by dissolving in a solvent mixture such as chloroform/diethyl ether and adding a solution of hydrogen chloride in dioxane. Evaporation of the solvents yields the product as the hydrochloride.

EXAMPLE 4

The compound of Table 1, wherein R is —(CH$_2$)$_n$—O—CH$_2$—COOH and wherein —A—B— has the formula —CO—CH$_2$—, and wherein n=2, is prepared from the compound of Table 1, wherein R is —(CH$_2$)$_n$OH and wherein —A—B— has the formula —CO—CH$_2$—, and wherein n=2, by treatment with a haloacetic acid, X—CH$_2$COOH, where X=chloro or bromo, in presence of a basic catalyst such as potassium carbonate in a solvent such as DMF with stirring with or without heating to cause reaction. After removal of the solvent by evaporation, the residue is mixed with water, the solution neutralized to pH 5–6, and the aqueous solution is extracted with an organic solvent such as chloroform, methylene chloride or ethyl acetate. After removal of the organic solvent by evaporation, the product may be purified by crystallization from a solvent such as methanol or ethanol. Similar compounds, where n=3–6, may be prepared by the same method from the compounds of Table 1, wherein R is —(CH$_2$)$_n$—O—CH$_2$—COOH and wherein —A—B— has the formula —CO—CH$_2$—, and wherein n=3–6.

Alternatively, the compounds of Table 1, wherein R is —(CH$_2$)$_n$—O—CH$_2$—COOH and wherein —A—B— has the formula —CO—CH$_2$—, and wherein n=2–6, may be synthesized according to the general method described under "Example 5", below.

EXAMPLE 5

The compound of Table 1, wherein R is —(CH$_2$)$_n$—O—CH$_2$—COOH and wherein —A—B— has the formula —CH$_2$—CO—, and wherein n=2, was prepared in two steps. In the first step 1.9 grams of Compound (2) was treated with (2-chloroethoxy)acetonitrile (2 equivalents) and potassium carbonate (2.4 equivalents) in 10 ml of dimethylformamide. After stirring for four days at room temperature, the solvent was evaporated in vacuo and 10 ml of water was added to the residue. The resulting suspension was extracted with 3×10 ml portions of chloroform, the combined extracts were evaporated and the crude product was purified by chromatography on silica gel with 2% methanol in chloroform as eluent. The intermediate, N-[(2-cyanomethoxy)ethyl]norketotifen (0.75 gram) was heated in concentrated hydrochloric acid for twelve hours. The solvent was evaporated in vacuo, and the pink residue was dissolved in methanol, treated twice with activated carbon, filtered, and the solvent was evaporated in vacuo, giving the hydrochloride of Example 5 (n=2) as a pink foam. Yield 0.71 gram. Proton NMR was consistent with the proposed structure.

EXAMPLE 6

The compound of Table 1, wherein R is —(CH$_2$)$_n$—O—CH$_2$—COOH and wherein —A—B— has the formula —CH$_2$—CH$_2$—, and wherein n=2, is prepared from the compound of Table 1, wherein R is —(CH$_2$)$_n$OH and wherein —A—B— has the formula —CH$_2$—CH$_2$—, and wherein n=2, by treatment with a haloacetic acid, X—CH$_2$COOH, where X=chloro or bromo, in presence of a basic catalyst such as potassium carbonate in a solvent such as DMF with stirring with or without heating to cause reaction. After removal of the solvent by evaporation, the residue is mixed with water, the solution neutralized to pH 5–6, and the aqueous solution is extracted with an organic solvent such as chloroform, methylene chloride or ethyl acetate. After removal of the organic solvent by evaporation, the product may be purified by crystallization from a solvent such as methanol or ethanol. Similar compounds, where n=3–6, may be prepared by the same method from the compounds of Table 1, wherein R is —(CH$_2$)$_n$OH and wherein —A—B— has the formula —CH$_2$—CH$_2$—, and wherein n=3–6, Alternatively, the compounds of Table 1, wherein R is —(CH$_2$)$_n$—O—CH$_2$—COOH and wherein —A—B— has the formula —CH$_2$—CH$_2$—, and wherein n=2–6, may be synthesized according to the general method described under "Example 5".

EXAMPLE 7

The compound of Table 1, wherein R is —(CH$_2$)$_n$OH and wherein —A—B— has the formula —CHOH—CH$_2$—, and wherein n=2, is prepared from the compound of Table 1, wherein R is —(CH$_2$)$_n$OH and wherein —A—B— has the formula —CO—CH$_2$—, and wherein n=2, by treatment with sodium borohydride in a solvent such as ethanol at room temperature. After decomposition of excess reagent with acetone, the solvents are removed by evaporation and the residue is crystallized from a solvent such as methanol or ethanol, with or without diethyl ether. Similar compounds, where n=3–6, may be prepared by the same method from the compounds of Table 1, wherein R is —(CH$_2$)$_n$OH and wherein —A—B— has the formula —CO—CH$_2$—, and wherein n=3–6.

The products may be converted to the hydrochloride salts by dissolving in a solvent mixture such as chloroform/diethyl ether and adding a solution of hydrogen chloride in dioxane. Evaporation of the solvents yields the product as the hydrochloride.

EXAMPLE 8

The compound of Table 1, wherein R is —(CH$_2$)$_n$—O—CH$_2$—COOH and wherein —A—B— has the formula —CHOH—CH$_2$—, and wherein n=2, is prepared from the compound of Table 1, wherein R is —(CH$_2$)$_n$OH and wherein —A—B— has the formula —CO—CH$_2$—, and wherein n=2, by treatment with sodiumborohydride in a solvent such as ethanol at room temperature. After decomposition of excess reagent with acetone, the solvents are removed by evaporation, and the residue is mixed with water, the solution neutralized with an acid such as dilute hydrochloric acid, and extracted with a solvent such as ethyl acetate. After removal of the organic solvent by evaporation, the residue is crystallized from a solvent such as methanol or ethanol, with or without diethyl ether. Similar compounds, where n=3–6, may be prepared by the same method from the compounds of Table 1, wherein R is —(CH$_2$)$_n$OH and wherein —A—B— has the formula —CO—CH$_2$—, and wherein n=3–6.

Alternatively, the compounds of Table 1, wherein R is —(CH$_2$)$_n$—O—CH$_2$—COOH and wherein —A—B— has the formula —CHOH—CH$_2$—, and wherein n=2–6, may be synthesized according to the general method described under "Example 5".

EXAMPLE 9

The compound of Table 1, wherein R is —(CH$_2$)$_n$OH and wherein —A—B— has the formula —CH$_2$—CHOH—, and wherein n=2, is prepared from the compound of Table 1, wherein R is —(CH$_2$)$_n$OH and wherein —A—B— has the formula —CH$_2$—CO—, and wherein n=2, by treatment with sodium borohydride in a solvent such as ethanol at room temperature. After decomposition of excess reagent with acetone, the solvents are removed by evaporation and the residue is crystallized from a solvent such as methanol or ethanol, with or without diethyl ether. Similar compounds, where n=3–6, may be prepared by the same method from the compounds of Table 1, wherein R is —$(CH_2)_nOH$ and wherein —A—B— has the formula —$CH_2CO$—, and wherein n=3–6.

The products may be converted to the hydrochloride slats by dissolving in a solvent mixture such as chloroform/diethyl ether and adding a solution of hydrogen chloride in dioxane. Evaporation of the solvents yields the product as the hydrochloride.

EXAMPLE 10

The compound of Table 1, wherein R is —$(CH_2)_n$—O—$CH_2$—COOH and wherein —A—B— has the formula —$CH_2$—CHOH—, and wherein n=2, is prepared from the compound of Table 1, wherein R is —$(CH_2)_n$—O—$CH_2$—COOH and wherein —A—B— has the formula —$CH_2$—CO—, and wherein n=2, by treatment with sodiumborohydride in a solvent such as ethanol at room temperature. After decomposition of excess reagent with acetone, the solvents are removed by evaporation, and the residue is mixed with water, the solution neutralized with an acid such as dilute hydrochloric acid, and extracted wit ha solvent such as ethyl acetate. After removal of the organic solvent by evaporation, the residue is crystallized from a solvent such as methanol or ethanol, with or without diethyl ether. Similar compounds, where n=3–6, may be prepared by the same method from the compounds of Table 1, wherein R is —$(CH_2)_n$—$CH_2$—COOH and wherein —A—B— has the formula —$CH_2$—CO—, and wherein n=3–6.

Alternatively, the compounds of Table 1, wherein R is —$(CH_2)_n$—O—$CH_2$—COOH and wherein —A—B— has the formula —$CH_2$—CHOH—, and wherein n=2–6, may be synthesized according to the general method described under "Example 5".

EXAMPLE 11

The compound of Table 1, wherein R is —$(CH_2)_nOH$ and wherein —A—B— has the formula —CO—CO—, and wherein n=2, is prepared by treatment of starting compound (4) with a 2-haloethanol, such as 2-bromoethanol or 2-chloroethanol, in presence of a basic catalyst such as potassium carbonate in a solvent such as N,N-dimethylformamide (DMF) with stirring with or without heating to cause reaction. After removal of the solvent by evaporation, the residue is mixed with water and extracted with an organic solvent such as chloroform, methylene chloride or ethyl acetate. After removal of the organic solvent by evaporation, the product may be purified by crystallization from a solvent such as methanol or ethanol. Similar compounds, where n=3–6, may be prepared by the same method but with ω-halo alcohols, X—$(CH_2)_{3-6}$—OH, where X is chloro or bromo.

The products may be converted to the hydrochloride slats by dissolving in a solvent mixture such as chloroform/diethyl ether and adding a solution of hydrogen chloride in dioxane. Evaporation of the solvents yields the product as the hydrochloride.

EXAMPLE 12

The compound of Table 1, wherein R is —$(CH_2)_n$—O—$CH_2$—COOH and wherein —A—B— has the formula —CO—CO—, and wherein n=2, is prepared from the compound of Table 1, wherein R is —$(CH_2)_nOH$ and wherein —A—B— has the formula —CO—CO—, and wherein n=2, by treatment with a haloacetic acid, X—$CH_2COOH$, where X=chloro or bromo, in presence of a basic catalyst such as potassium carbonate in a solvent such as DMF with stirring with or without heating to cause reaction. After removal of the solvent by evaporation, the residue is mixed with water, the solution neutralized to pH 5–6, and the aqueous solution is extracted with an organic solvent such as chloroform, methylene chloride or ethyl acetate. After removal of the organic solvent by evaporation, the product may be purified by crystallization from a solvent such as methanol or ethanol. Similar compounds, where n=3–6, may be prepared by the same method from the compounds of Table 1, wherein R is —$(CH_2)_nOH$ and wherein —A—B— has the formula —CO—CO—, and wherein n=3–6.

Alternatively, the compounds of Table 1, wherein R is —$(CH_2)_n$—O—$CH_2$—COOH and wherein —A—B— has the formula —CO—CO—, and wherein n=2–6, may be synthesized according to the general method described under "Example 5".

EXAMPLE 13

The compound of Table 1, wherein R is —$(CH_2)_nOH$ and wherein —A—B— has the formula —CHOH—CHOH—, and wherein n=2, is prepared from the compound of Table 1, wherein R is —$(CH_2)_nOH$ and wherein —A—B— has the formula —CO—CO—, and wherein n=2, by treatment with sodium borohydride in a solvent such as ethanol at room temperature. After decomposition of excess reagent with acetone, the solvents are removed by evaporation and the residue is crystallized from a solvent such as methanol or ethanol, with or without diethyl ether. Similar compounds, where n=3–6, may be prepared by the same method from the compounds of Table 1, wherein R is —$(CH_2)_nOH$ and wherein —A13 B— has the formula —CO—CO—.

The products may be converted to the hydrochloride salts by dissolving in a solvent mixture such as chloroform/diethyl ether and adding a solution of hydrogen chloride in dioxane. Evaporation of the solvents yields the product as the hydrochloride.

EXAMPLE 14

The compound of Table 1, wherein R is —$(CH_2)_n$—O—$CH_2$—COOH and wherein —A—B— has the formula —CHOH—CHOH—, and wherein n=2, is prepared from the compound of Table 1, wherein R is —$(CH_2)_n$—O—$CH_2$—COOH and wherein —A—B— has the formula —CO—CO—, and wherein n=2, by treatment with sodium borohydride in a solvent such as ethanol at room temperature. After decomposition of excess reagent with acetone, the solvents are removed by evaporation, and the residue is mixed with water, the solution neutralized with an acid such as dilute hydrochloric acid, and extracted with a solvent such as ethyl acetate. After removal of the organic solvent by evaporation, the residue is crystallized from a solvent such as methanol or ethanol, with or without diethyl ether. Similar compounds, where n=3–6, may be prepared by the same method from the compounds of Table 1, wherein R is —$(CH_2)_n$—O—$CH_2$—COOH and wherein —A—B— has the formula —CO—CO—.

Alternatively, the compounds of Table 1, wherein R is —$(CH_2)_n$—O—$CH_2$—COOH and wherein —A—B— has the formula —CHOH—CHOH—, and wherein n=2–6, may be synthesized according to the general method described under "Example 5".

The present invention provides the compounds described above, including the isomers of the racemic compounds, and the pharmaceutically acceptable acid addition salt and solvates of the new compounds.

The optically active isomers of the compounds of this invention can be prepared by the resolution of the racemate using conventional means such as fractional crystallization of diastereomeric salts with chiral acids. Other standard methods of resolution known to those skilled in the art, include, but are not limited to, crystallization and chromatography on a chiral substrate and can also be used. The optically active isomers of the present invention may also be prepared by stereoselective synthesis.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrogen fumarate is particularly preferred.

The present invention also provides pharmaceutical compositions, which comprise one or more compounds of the invention, formulated together with one or more pharmaceutically acceptable carriers. The pharmaceutical compositions may be specially formulated for oral administration, conjunctival instillation, sublingual administration, parenteral administration, transdermal administration, rectal administration, buccal administration, or for topical administration, or for administration by inhalation, insufflation of powder or aerosol.

Pharmaceutical compositions of this invention can be administered to humans and other mammals orally, sublingually, parenterally, cutaneously, transdermally, rectally, buccally, topically, by conjunctival instillation, or as an oral or nasal spray or aerosol. The term "parenteral" administration includes intravenous, intraarterial, intramuscular, intraperitoneal, intracutaneous, subcutaneous or intraarticular injection and infusion. The tern "transdermal" includes the use of various devices ("patches" etc.) that can facilitate or modify the transport or absorption of the drug through skin.

Oral administration forms

Pharmaceutical compositions of this invention for oral administration of solid dosage forms, include capsules, granules, pills, powders, and tablets. In such solid dosage forms, the active compound may be mixed with one or more pharmaceutically acceptable excipients or carriers (ex. sodium citrate, dicalcium phosphate), fillers or extenders (ex starch, lactose, sucrose, glucose, mannitol, silicic acid), binders (ex. carboxymethylcellulose, alginates, gelatin, polyvinylpyrrolidone, sucrose, acacia), humectants (ex. glycerol), solution retarding agents (ex. paraffin), disintegrating agents (ex. agar-agar, calcium carbonate, starch, alginic acid, silicates, sodium carbonate), absorption accelerators (ex. quarternary ammonium compounds), wetting agents (ex. cetyl alcohol, glycerol monostearate), absorbents (ex. kaolin, bentonite clay), lubricating agents (ex. talk, calcium stearate, magnesium stearate, polyethylene glycols, sodium lauryl sulfate), and/or buffering agents.

Solids forms of capsules, dragees, granules, pills, and tablets can have coatings and/or shells (ex. enteric coatings) known in the pharmaceutical formulating art. The compositions may also be designed to release the active ingredient(s) in a certain part of the gastro-intestinal tract or in a controlled release, slow-release or in a delayed-release manner.

The composition may also be designed for lymphatic absorption of the active ingredient(s).

The active compound(s) can also be micro-encapsulated with one or more of the above-mentioned excipients.

Liquid dosage forms for oral administration include pharmaceutically acceptable emulsions, solutions, suspensions, syrups and elixirs. The liquid dosage form may also contain commonly known diluents (ex. water, other solvents, solubilizing agents), emulsifiers (ex. ethanol, isopropyl alcohol, ethyl carbonate, ethyl acetate, benzyl alcohol, benzyl benzoate, propylene glycol, butylene glycole, dimethyl formamide, oils, oleic acid, glycerol, polyethylene glycols, sorbitan fatty esters, and mixtures thereof.

Besides inert diluents, the oral compositions can also include adjuvants such as wetting, emulsifying, suspending, sweetening, or flavoring agents.

Suspensions may contain one or more suspending agents known in the pharmaceutical formulating art.

Topical administration forms (including forms for conjunctival instillation)

Compositions for topical administration of the compounds of this invention include solutions, suspensions, droplets, sprays, ointments and powders.

In addition to the therapeutically active ingredients, the composition of this invention for topical ocular or conjunctival administration may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, ONAMER M and other agents, known to those skilled in the art. Such preservatives, if utilized, will typically be employed in an amount from 0.001% to 1.0% by weight (wt. %). Examples of suitable agents which may be utilized to adjust the tonicity or osmolality of the formulations include sodium chloride, potassium chloride, mannitol, dextrose glycerin and propylene glycol. Such agents, if utilized, will be employed in an amount of 0.1% to 10.0% by weight (wt. %). The compositions are preferably aqueous, and have a pH in the range of 3.5 to 8.0 and an osmolality in the range of 280 to 320 millimoles per liter.

As realized by those skilled in the art, compositions may be formulated in various dosage forms suitable for topical ophthalmic delivery, including solutions, suspensions, emulsions, gels, and erodible solid ocular inserts.

Parenteral administration forms

Pharmaceutical compositions for parenteral injections include pharmaceutically acceptable sterile aqueous or non-aqueous solutions, dispersions, suspensions, emulsions and sterile powders for reconstitution into sterile injectable solutions or dispersions prior to use. Various aqueous and nonaqueous carriers, diluents solvents and vehicles may be used (ex. water, ethanol, glycerol, glycol), as well as vegetable oils (ex. olive oil), and organic esters (ex ethyl oleate), or mixtures thereof may be used. Fluidity can be maintained by use of coating material such as lecithin, by restricting particle size and by use of surfactants.

The compositions may also contain adjuvants such as preservatives, wetting agents, emulsifying agents, dispersing agents, antibacterial agents, antifungal agents, isotonic agents, and/or absorption-delaying agents. Absorption-prolonging or absorption-slowing effects may be achieved by injecting a crystalline or amorphous suspension with low water solubility. Delayed absorption may also be obtained by dissolving or suspending the drug in an oil vehicle or by using injectable depot forms (ex. microencapsulated matrices of the drug in biodegradable polymers, such as polylactide-polyglycolide, polyorthoesters, polyanhydrides) or by using various types of liposomes or microemulsions to hold the drug. Formulations for injection can be sterilized by various methods.

Rectal administration forms

Compositions for rectal administration are preferably suppositories.

Buccal administration forms

Compositions for buccal administration are preferably toothpastes, mouthwashes, sublingual preparations, chewing gums etc.

Sublingual administration forms

Various galenic formulations can be used: concentrated solutions or suspensions of the drug may be applied sublingually by various drop devices; various aerosol devices may be used to spray the drug onto the oral mucus membranes; specifically designed fast dissolving tablets, capsules or powders may as well be used for fast delivery of the full dose.

Transdermal administration forms

Compositions for transdermal administration of the compounds of this invention include various known patches, bandages etc.

Oral or nasal spray or droplet administration

Compositions for oral or nasal sprays or droplets may be in the form of solutions, suspensions or dry powders and may be designed for nasal, buccal, bronchial/pulmonary, and/or gastric absorption of the drug.

Therapeutic dose levels

The actual dosage levels of active ingredients in the pharmaceutical compositions of this inventions may be varied so as to obtain the desired therapeutic effect. Thus the amount of drug used varies and may depend on factors such as administration form, severity of the disease, frequency of dosing etc. For use as medication to patients suffering from benign airways or bronchial disorders (such as asthma, bronchitis, etc.), oral doses of the compound of this invention are used at dose levels of 0.5 mg to about 200 mg, preferably from 0.5 mg to 10 mg once to four times daily to a patient weighing 60 kg. The daily dose may be increased or decreased depending on various factors, for example the weight and the disease status of the patient.

As an example, for use as medication to patients suffering from allergic conjunctivitis oral doses of the compound of this invention are used at dose levels of 0.1 mg to about 100 mg, preferably from 0.2 mg to 10 mg once to four times daily to a patient weighing 60 kg. For patients suffering from seasonal allergic conjunctivitis, the concentration of norketotifen solution for instillation in to the conjunctival sac ranges from 0.01% to 2.0%, preferably 0.02% to 1.0%. The frequency and amount of the dosage will be determined by the clinician based on various clinical factors, such as for example the weight and the severity of the disease of the patient. The use will typically comprise topical application of one to two drops (or an amount of a solid or semisolid dosage form) to the affected eye one to four times per day.

Oral unit dosage formulation

EXAMPLE 15

Tablet formulations

| Ingredients | per tablet | per batch of 10,000 tablets |
|---|---|---|
| Compound of Example 5 | 2 mg | 20 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The active ingredient (in this example, the compound of Example 5, where n=2) is blended with the lactose and cellulose until a uniform blend is formed. The lake is added and further blended. Finally, the calcium stearate is blended in, and the resulting mixture is compressed into tablets using a 9/32 inch (7 mm) shallow concave punch. Tablets of other strengths may be prepared by altering the ration of active ingredient to the excipients or to the final weight of the tablet.

This invention provides methods for the treatment and/or prophylaxis of all forms of bronchial asthma, allergic bronchitis, multi-system allergies, allergic rhinitis, and allergic skin disorders in mammals, such as humans, while avoiding the sedating side effects and other toxic manifestations of ketotifen. These methods comprise administering to the mammal in need of such treatment and/or prophylaxis, effective amounts of at least one compound of the invention or a pharmaceutically acceptable salt thereof.

This invention also provides methods for co-administration one or more compounds of the invention with adrenergic beta-receptor agonists, including but not limited to albuterol, terbutaline, fenoterol, formoterol or salmeterol, thereby eliminating or decreasing bronchial hyperreactivity that may be induced by said beta-agonist therapy. The invention also provides methods for co-administration of a compound of this invention with other agents or drugs causing bronchial hyperreactivity, including but not limited to adrenergic beta-receptor blocking agents or cyclooxygenase inhibitors, thereby eliminating or decreasing the bronchial hyperreactivity that is induced by such therapy.

This invention provides methods for treatment and/or prophylaxis of forms of ocular diseases such as allergic conjunctivitis or allergic keratitis and inflammatory diseases such as blepharitis, conjunctivitis, episcleritis, scleritis, keratitis, anterior uveitis, posterior uveitis, endophthalmitis, optic neuritis, cranial arteritis, sympathetic ophthalmia in mammals, such as humans, while avoiding ocular irritation, sedation and other toxic manifestations of ketotifen and steriods. These methods comprise administering to the mammal in need of such treatment and/or prophylaxis, effective amounts of a compound of this invention, or of a pharmaceutically acceptable salts thereof.

This invention also provides methods for co-administration of a compound of this invention, with at least one drug of the following classes: ocular antihypertensive agents, adrenergic agonists or antagonists, antibacterial agents, antiviral agents, steroids, cyclooxygenase inhibitors, leukotriene antagonists, lipoxygenase inhibitors and other ocular therapeutic remedies. In particular, the present invention provides for co-administration of a compound of this invention with ophthalmic decongestants, such as for example phenylephedrine, naphazoline, tetrahydrozoline or with antibacterial agents, such as bacitracin, neomycin and polymyxin.

The invention also provides methods for administration of a compound of this invention in conjunction with surgical procedures to minimize inflammation or irritation and improve the postsurgical healing process.

This invention provides methods for treatment and/or prophylaxis of forms of gastroenterological diseases such as hypersecretory syndromes including Zollinger-Ellison syndrome, gastric irritation, enteritis, gastric or duodenal ulcers, acid indigestion, heartburn or undesired gastric acid secretion. These methods comprise administering to the mammal in need of such treatment and/or prophylaxis, effective amounts of a compound of this invention, or of a pharmaceutically acceptable salts thereof.

EQUIVALENTS

Those skilled in the art will recognize, or be able to ascertain, using no more than routine experimentation, many equivalents to the specific embodiments of the invention described herein. Such equivalents include the therapeutic use of a single isomer and a composition containing same, while avoiding the side effects residing in the corresponding isomer(s). Such equivalents also include numerous pharmaceutically acceptable salt forms e.g. sulfate, hydrobromide, hydrochloride, dihydrochloride, fumarate, methanesulphonate, hydroxynaphthoate or where appropriate one or other of the hydrate forms thereof, see Merck Index 11th edition (1989) items 9089, 209, 3927, 4628, 8223, 5053, 5836, 8142, 2347, 7765, 1840, 9720, 7461, 1317, 4159, and 963 and references cited therein and Am. Rev. Resp. Dis. 1988, 137: (4,2/2) 32. Such equivalents also include the co-administration of at least one compound of the present invention with any other drug that is used to combat diseases in mammals, mentioned in this document. Those skilled in the art of medicine may also realize that higher or lower doses than those indicated here may be preferred and the doses may be given more or less frequently than suggested here.

Those skilled in the art of pharmacology, may realize that the compounds of the invention, having certain pharmacological properties (such as antihistaminic activity on various receptor types, PAF-antagonistic activity, mast cell stabilizing activity etc.) may be useful for other indications than those listed here. Such indications are equivalents to the specific embodiments of the invention described herein.

Those skilled in the art will realize that by using a single isomer (customer) of any of the racemic compounds of the invention or of norketotifen or of 10-OH-norketotifen, it is possible to avoid side effects residing in the other isomer. Such side effects may include for example cardiovascular side effects, such as for example cardiodepression, or CNS side effects, such as for example sedation. All equivalents are intended to be included in this present invention.

What is claimed is:
1. A compound having the formula:

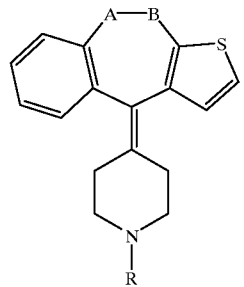

including stereochemically isomeric forms thereof and pharmaceutically acceptable salts thereof, wherein:

R is a member selected from the group consisting of hydroxyC$_{2-6}$alkyl and carboxyC$_{1-6}$alkyloxyC$_{1-6}$alkyl, and —A—B— is a moiety having the formula

| | |
|---|---|
| —CO—CH$_2$— | (a) |
| —CH$_2$—CO— | (b) |
| —CH$_2$—CH$_2$— | (c) |
| —CHOH—CH$_2$— | (d) |
| —CHOH—CHOH— | (e) |
| —CH$_2$—CHOH— | (f) | or

| | |
|---|---|
| —CO—CO— | (g). |

2. A compound according to claim 1, wherein —A—B— has the formula —CH$_2$—CO— or a pharmaceutically acceptable salt thereof.

3. A compound according to claim 1, wherein R is —(CH$_2$)$_n$OH, and wherein —A—B— has the formula —CH$_2$—CO—, and wherein n is 2 to 6, or a pharmaceutically acceptable salt thereof.

4. A compound according to claim 1, wherein R is —(CH$_2$)$_n$—O—(CH$_2$)$_n$—COOH, and wherein —A—B— has the formula —CH$_2$—CO—, and wherein n is 1 to 6, or a pharmaceutically acceptable salt thereof.

5. A method for preventing or treating allergic disorders, which comprises administering to a mammal in need of such treatment a therapeutically effective amount of a compound of claim 1.

6. The method of claim 5 wherein said allergic disorder is selected from the group consisting of allergic rhinitis, bronchitis, urticaria, atopic dermatitis, and enteritis.

7. A method for preventing or treating ocular disorders, which comprises administering to a mammal in need of such treatment a therapeutically effective amount of a compound of claim 1.

8. The method of claim 7, wherein said ocular disorder is selected from the group consisting of anterior uveitis, blepharitis, conjunctivitis, cranial arteritis, endophthalmitis, episcleritis, keratitis, keratoconjunctivitis, optic neuritis, posterior uveitis, retinopathy and scleritis.

9. A method for preventing or treating respiratory disorders, which comprises administering to a mammal in need of such treatment a therapeutically effective amount of a compound of claim 1.

10. The method of claim 9, wherein said respiratory disorder is selected from the group consisting of chronic obstructive pulmonary disease (COPD), asthma, cough and bronchitis.

11. A method for preventing or treating smooth muscle hyperreactivity which comprises administering to a mammal in need of such treatment a therapeutically effective amount of a compound of claim 1.

12. A method for preventing or treating gastro-intestinal disorders, which comprises administering to a mammal in need of such treatment a therapeutically effective amount of a compound of claim 1.

13. The method of claim 12, wherein the said gastro-intestinal disorder is selected from the group consisting of hypersecretory syndrome, the Zollinger-Ellison syndrome, gastric irritation, enteritis, gastric ulcer, acid indigestion and heartburn.

14. A method wherein a compound as defined in claim 1 is administered to a mammal by inhalation, or by conjunctival instillation, or by nasal insufflation or by parenteral, transdermal, buccal, rectal, sublingual, nasal, topical or oral administration.

15. The method according to claim 14, wherein a compound as defined in claim 1 is administered to a mammal in a delayed, extended or otherwise controlled release formulation.

16. A method wherein a compound as defined in claim 1 is administered to a mammal from about 0.2 mg to about 200 mg, preferably 0.5 mg to 20 mg once to four times daily to a patient weighing 60 kg.

17. The method of claim 7, wherein a compound as defined in claim 1 is administered by conjunctival instillation of a solution containing from about 0.01% to 2.0%, one to four times daily.

18. A solid, semi-solid, liquid, suspension, aerosol or transdermal pharmaceutical composition, comprising a therapeutically effective amount of a compound as defined in claim 1, in combination with pharmaceutically acceptable carrier or carrier system.

19. A method comprising administering to a mammal in need thereof a composition, said composition comprising a therapeutically active amount of a compound as defined in claim 1, together with one or more drugs of the class consisting of analgesics, antibacterial agents, antiinflammatory agents, decongestants, vasoconstrictors, vasodilators, cough suppressants and expectorants.

20. A method comprising administering topically to an eye of a mammal in need thereof a composition, said composition comprising a therapeutically active amount of a compound as defined in claim 1, together with one or more drugs of the class consisting of cholinergic agents, anti-muscarinic agents, choline esterase inhibitors, adrenergic beta-receptor blocking agents, anti-bacterial agents, sympathomimetics, carbonic anhydrase inhibitors, antiinflammatory agents, decongestants, astringents, viscosity-adjusting substances and topical anesthetics.

* * * * *